(12) United States Patent
Primus et al.

(10) Patent No.: US 7,838,573 B2
(45) Date of Patent: Nov. 23, 2010

(54) GUTTA-PERCHA COMPOSITIONS FOR OBTURATING DENTAL ROOT CANALS

(75) Inventors: Carolyn M. Primus, Bradenton, FL (US); James L. Gutmann, Dallas, TX (US)

(73) Assignee: DENTSPLY International, Inc., York, PA (US)

(*) Notice: Subject to any disclaimer, the term of this patent is extended or adjusted under 35 U.S.C. 154(b) by 630 days.

(21) Appl. No.: 11/823,285

(22) Filed: Jun. 27, 2007

(65) Prior Publication Data

US 2008/0085948 A1    Apr. 10, 2008

Related U.S. Application Data

(60) Provisional application No. 60/819,160, filed on Jul. 7, 2006.

(51) Int. Cl.
| | |
|---|---|
| A61K 6/02 | (2006.01) |
| A61K 6/06 | (2006.01) |
| A61K 6/08 | (2006.01) |
| A61L 24/02 | (2006.01) |
| A61C 5/04 | (2006.01) |
| A61C 5/02 | (2006.01) |
| A61C 5/00 | (2006.01) |

(52) U.S. Cl. .............. 523/116; 523/113; 523/114; 523/115; 523/117; 433/224; 433/226; 433/228.1; 106/35

(58) Field of Classification Search ........... 433/224, 433/226, 228.1; 523/116, 117, 113, 114; 523/115; 106/35
See application file for complete search history.

(56) References Cited

U.S. PATENT DOCUMENTS

| | | | | |
|---|---|---|---|---|
| 5,415,547 | A | | 5/1995 | Torabinejad et al. |
| 5,540,766 | A | * | 7/1996 | Castellani ............... 106/35 |
| 5,648,403 | A | * | 7/1997 | Martin ................. 523/117 |
| 5,769,638 | A | | 6/1998 | Torabinejad et al. |
| 5,925,179 | A | * | 7/1999 | Mannschedel ........... 106/35 |
| 2003/0159618 | A1 | | 8/2003 | Primus |
| 2004/0226478 | A1 | | 11/2004 | Primus |
| 2005/0263036 | A1 | | 12/2005 | Primus |
| 2007/0098811 | A1 | * | 5/2007 | Lu et al. ................ 424/602 |

FOREIGN PATENT DOCUMENTS

WO    WO 2005087178 A1 *  9/2005

* cited by examiner

*Primary Examiner*—Mark Eashoo
*Assistant Examiner*—Michael Pepitone
(74) *Attorney, Agent, or Firm*—Douglas J. Hura; David A. Zdurne; Leana Levin

(57) ABSTRACT

Improved compositions comprising a mixture of gutta-percha and a hydraulic material containing calcium silicate, calcium aluminate, calcium phosphate, and calcium sulfate compounds are provided. Preferably, the composition includes hydroxylapatite mineral. The composition is particularly suitable for obturating and sealing dental root canals. The composition should provide a stable barrier to bacterial and fluid leakage in the root canal system of a tooth. In addition, the composition should help promote the growth of new bone and tissue surrounding the root tip area.

11 Claims, 1 Drawing Sheet

Particle size distribution of Dentalcrete

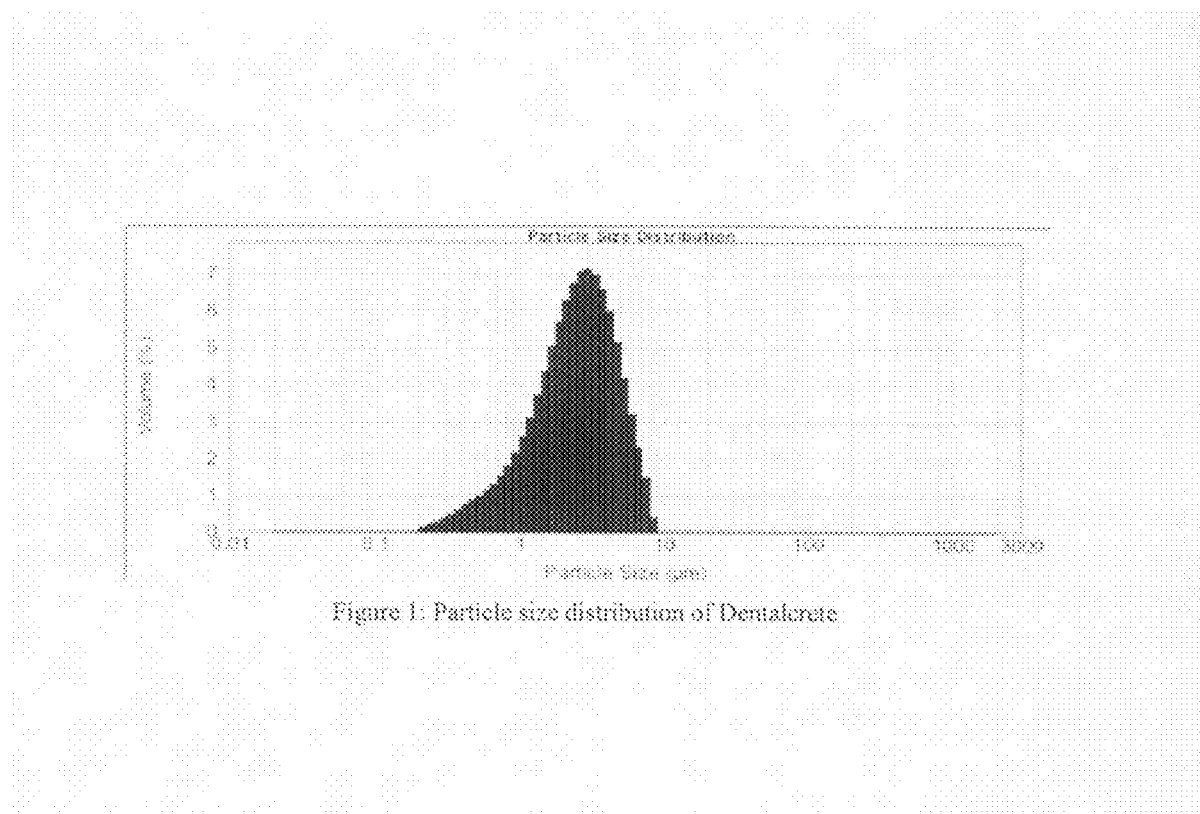
Figure 1: Particle size distribution of Dentalcrete

GUTTA-PERCHA COMPOSITIONS FOR OBTURATING DENTAL ROOT CANALS

CROSS-REFERENCE TO RELATED APPLICATIONS

This application claims the benefit of U.S. Provisional Patent Application Ser. No. 60/819,160 having a filing date of Jul. 7, 2006, the entire contents of which are hereby incorporated by reference.

BACKGROUND OF THE INVENTION

1. Field of the Invention

The present invention relates generally to improved dental compositions for obturating and sealing root canals in a tooth. The compositions contain a mixture of gutta-percha and other components. Methods for filling and sealing root canals using the composition are also provided.

2. Brief Description of the Related Art

The inner portion of a tooth includes a pulp cavity that contains soft living tissue or the "pulp" of the tooth. The pulp includes connective tissue blood vessels that nourish the tooth, and nerve endings. Referring to a tooth in the mandibular jaw, the pulp cavity comprises an upper pulp chamber and root canals that extend downwardly to the apex or apical section of the tooth. In a healthy tooth, the enamel of the tooth is a very hard, calcium-based substance that covers the portion of the tooth seen in the mouth, which is known as the crown. Under the enamel is a hard layer of dentin tissue containing a matrix of minute tubules surrounds and protects the pulp. The enamel covers and protects the dentin in the upper portion (crown) of the tooth. The cementum of the tooth is a thin, mineralized tissue that covers and protects the outer surface of the root in the jaw. Dental decay or caries is typically caused by bacteria accumulating on teeth forming a biofilm (plaque). The plaque biofilm produce acids that dissolve or weaken the enamel, forming caries. When dental caries is found in the enamel portion of the tooth, a dental professional will remove the caries in order to prevent further decay of the tooth. In some instances, the dental caries may be so deep that it penetrates the enamel to the dentin tissue. At this point, the bacteria and other microorganisms can migrate rapidly into the pulp tissue causing infection and inflammation. As a result, abscesses or inflammation may form in the pulp and eventually the periapical tissues surrounding the apex or apical section of the tooth in the jawbone, where the teeth are set. The pulp cavity and surrounding bone and tissue may become exposed to infectious bacteria by actions other than decay such as deep cracks or other traumatic injuries to the tooth. Provided that the dental disease is not too progressive, dental professionals will use root canal treatment procedures to remove the damaged tissue from the tooth and replace it with an inert, biocompatible material.

The root canal system of a tooth is complex and many treatment methods can be used depending upon the condition of the patient and the practitioner. In general, root canal treatment methods first involve drilling an opening in the crown of the tooth to provide access to the pulp. Then, endodontic files are used to thoroughly remove the pulp tissue from the pulp chamber and root canals. The files are also used to shape the canals. Next an irrigant may be used to remove residual debris and the smear layer created by the files. The root canal walls are coated with a sealer and then the canals are filled with an inert filling material. This sealing and filling of the roots ideally prevents bacteria and other microorganisms from re-entering and causing infection of the living tissue surrounding the root tip. As a final step, the pulp chamber and opening in the crown of the tooth are filled with a dental restoration such as a composite material. Preferably a permanent restoration with a synthetic crown of metal or ceramic, perhaps including a post for stability, is placed in the tooth. The permanent restoration is normally fabricated after the root canal procedure.

Gutta-percha is a naturally occurring and synthesized isomer of rubber often used to fill and seal the pulp chamber and root canals. Gutta-percha points having a tapered conical shape can be prepared, and these points can be fitted into the root canal. Such gutta-percha points are advantageous, because the tapered shape of the gutta-percha point means that it can assume the tapered shape created by the endodontic files used in the root canal. Historically, one treatment method involved using cold single cones of gutta-percha. In this method, zinc oxide-eugenol cement sealer was first placed in the root canal. Then a single cone of gutta-percha, without lateral condensation, was fitted into the root canal. Subsequently, a cold lateral condensation technique was developed. This technique involved compressing a series of gutta-percha cones into the root canal. A zinc oxide-eugenol cement sealer also was used in this procedure. The filling would essentially comprise multiple gutta-percha cones tightly pressed together in a matrix of dental cement. While this procedure created a more three-dimensional filling of the root canal system, there were still some disadvantages including the possible occurrence of voids or open spaces in the root canal.

More recently, procedures employing heated gutta-percha have been used. Plasticizing the gutta-percha allows it to flow so that it can move into the minute intra-canal spaces, lateral canals, accessory canals, anastomoses, and other irregularities of the canals. Various thermoplastic heating techniques have been developed. In one technique, an instrument with a cannula containing the gutta-percha is used. The cannula is preheated and the needle of the cannula is inserted into the root canal to a predetermined depth. However, it has been found that one problem with heated gutta-percha is that it flows only a small amount and shrinks upon cooling. Combinations of cold and warm gutta-percha techniques are commonly used.

Another technique uses a metal or plastic carrier coated with a layer of gutta-percha. The carrier includes a metal or plastic shaft with a distal tapered end that extends from a handle. The gutta-percha coated carrier is commonly referred to as an endodontic obturator in the dental field. One example of such an endodontic obturator is available from Dentsply Tulsa Dental Specialties (Tulsa, Okla.) under the brand name, THERMAFIL. In practice, the endodontic obturator is first heated in an oven. This heating step plasticizes the gutta-percha. Then, the heated obturator is inserted into the previously cleaned and shaped root canal. The carrier transports the gutta-percha to the working length of the canal and laterally compacts the gutta-percha into lateral and accessory canals. Once the carrier is stabilized in the canal, the upper handle portion and shaft is severed at a point level to the orifice of the canal using a dental bur or other instrument. The lower portion of the shaft remains in the canal encased in the hardened gutta-percha.

Other known materials can be used for treating root canals. For example, compositions containing hydraulic cement can be used, such as portland cement. In general, portland cement contains a dicalcium silicate, tricalcium silicate and usually calcium aluminate, tetracalcium aluminoferrite, and calcium sulfate. Portland cement is commonly gray, but white versions, with lower iron content are known. The chemical composition and physical properties of such cement compositions must be suitable for dental applications.

For example, Torabinejad et al., U.S. Pat. Nos. 5,769,638 and 5,415,547 disclose methods for sealing root canals and filling tooth cavities using a portland cement composition. In manufacturing the cement, the raw materials are crushed, ground, blended and fired to about 1500° C. After firing the cement clinker is ground, and a small amount of calcium sulfate is added to the cement to control the setting time.

Primus, US Patent Application Publication US2005/ 0263036 discloses a cement composition that is substantially free from iron oxide and has a calcium oxide content in the range of about 50 to about 75% by weight and a silica content in the range of about 15 to about 25% by weight.

A popular and effective material used in root canal treatment is ProRoot™ MTA root repair material available from Dentsply Tulsa Dental Specialties. ProRoot MTA material has a composition similar to portland cement, with the addition of bismuth oxide. Particularly, the ProRoot MTA material includes particles of tricalcium silicate, dicalcium silicate, tricalcium aluminate, tetracalcium aluminoferrite, calcium sulfate dihydrate, and bismuth oxide. ProRoot MTA material is used in a variety of clinical applications including repairing root canal perforations during root canal therapy; filling root ends; repairing root resorption; and apexification of deciduous teeth with immature open roots.

Although traditional gutta-percha compositions are generally effective in treating root canals, it would be desirable to have a more biocompatible composition. Ideally, the improved gutta-percha composition would promote healing of the bones and tissue surrounding the root canal tips and would enhance the seal against bacterial migration into the root canal. The present invention provides such improved gutta-percha compositions having these desirable properties as well as other beneficial features and advantages.

SUMMARY OF THE INVENTION

The present invention provides a composition for sealing a tooth root canal. The composition includes a mixture of about 10% to about 50% by weight of gutta-percha and about 1% to about 30% by weight of Dentalcrete material. By the term, "Dentalcrete" as used herein, it is meant a cement-like material comprising particles selected from the group consisting of tricalcium silicate, dicalcium silicate, tricalcium aluminate, tetracalcium aluminoferrite, calcium sulfate dihydrate, and radiopaque component, and mixtures thereof as described in further detail below. Suitable radiopaque components include bismuth oxide, barium sulfate, and radiopaque glass. The Dentalcrete material is in the form of powder particulate having an average particle size in the range of about 1 to about 40 µm and preferably about 1 to about 15 µm.

In a preferred embodiment, the composition further includes about 1 to about 20% by weight of hydroxylapatite mineral which helps bone and tissue growth. The invention further includes a method of treating root canals using this composition.

BRIEF DESCRIPTION OF THE FIGURES

FIG. 1 is a bar graph showing the particle size distribution of a preferred Dentalcrete material.

DETAILED DESCRIPTION OF THE PREFERRED EMBODIMENTS

The composition of this invention, which can be used to seal root canals in teeth, comprises a mixture of gutta-percha and other components. The composition should provide a stable barrier to bacterial and fluid leakage in the root canal system of a tooth.

Gutta-percha, an isomer of natural rubber, is a known material in the dental arts. Once warmed, gutta-percha softens and becomes a malleable material. Any suitable gutta-percha material can be used in accordance with this invention. The gutta-percha can be in a pure form or it can be blended with additives such as zinc oxide, dyes, lubricants, pigments, preservatives, waxes, titanium dioxide, and barium sulfate. The gutta-percha is normally present in the composition in an amount in the range of about 10% to about 50% by weight and preferably in the range of about 20% to about 30%.

The gutta-percha is blended with a material referred to herein as "Dentalcrete", and preferably other components are added to the blend as discussed further below. The amount of Dentalcrete material used in the composition is generally about 1% to about 30% by weight. The Dentalcrete material comprises fine hydrophilic particles selected from the group consisting of tricalcium silicate, dicalcium silicate, tricalcium aluminate, tetracalcium aluminoferrite, calcium sulfate dihydrate, and radiopaque material, and mixtures thereof. Preferably, the Dentalcrete material contains a finely ground radiopaque component such as, for example materials selected from the group consisting of bismuth oxide, barium sulfate, tantalum oxide, cerium oxide tin oxide, zirconium oxide compounds and radiopaque glasses containing tantalum, barium and strontium, and mixtures thereof.

The preferred Dentalcrete material has a composition similar to portland cement and sets in the presence of water to form a colloidal gel. When a small amount of water (less than 25% by weight) is added to the Dentalcrete material, it gives the composition a putty-like consistency. The putty is moldable, has good dimensional stability and solidifies to form a hard, rock-like material.

In a preferred embodiment, the Dentalcrete material comprises about 20 to about 80 wt. % tricalcium silicate ($3CaO \cdot SiO_2$); about 20 to about 50 wt. % dicalcium silicate ($2CaO \cdot SiO_2$); about 1% to about 20 wt. % tricalcium aluminate ($3CaO \cdot Al_2O_3$), and about 1 to about 20 wt. % tetracalcium aluminoferrite ($4CaO \cdot Al_2O_3 \cdot Fe_2O_3$); about 1 to about 20 wt. % calcium sulfate dihydrate ($CaSO_4 \cdot 2H_2O$), and about 1 to about 50 wt. % radiopaque component. More preferably, the Dentalcrete material contains about 20 to 40 wt. % bismuth oxide as a radiopaque component.

It should be understood that other Dentalcrete compositions can be used in accordance with this invention. For example, in another embodiment, a Dentalcrete material containing only dicalcium silicate or tricalcium silicate particles or mixtures thereof can be used.

The Dentalcrete material is in the form of powder particulate. In one preferred embodiment, the particle size of the powder particulate is reduced so that the average particle size is in the range of about 1 µm to about 40 µm and more preferably it is in the range of about 1 µm to about 10 µm as shown in FIG. 1. The particles in the Dentalcrete material can be finely milled or extra-finely milled as described in the Examples below. By the term, "finely milled," it is meant that the particles have a particle size distribution in the range of about 0.10 µm to about 60 µm. By the term, "extra-finely milled," it is meant that the particles have a particle size distribution in the range of about 0.10 µm to about 20 µm. Reducing the particle size of the powder helps to increase the viscosity and improve the handling properties of the final composition. Reduction of the particles can be achieved using suitable particle comminuting means known in the art.

In another preferred embodiment, hydroxylapatite, a calcium phosphate compound, $Ca_{10}(PO_4)6(OH)_2$ that is very similar in composition to bone, is added to the mixture of gutta-percha and Dentalcrete. Autogenous bone has two basic components, organic and inorganic. The inorganic component of autogenous bone is primarily hydroxylapatite, and the organic component is primarily collagen. It is believed that the hydroxylapatite powder should help promote healing of the bone and tissue surrounding the root tip. Hydroxylapatite is compatible with the gutta-percha and Dentalcrete materials and helps provide a stable platform for bone and tissue repair in the periapical tissue. In the improved gutta-percha/Dentalcrete/hydroxylapatite composition of the present invention, the hydroxylapatite component has the same mineral composition as human bone, thereby providing a natural scaffold for bone and tissue regeneration.

In another version, the gutta-percha mixture may be mixed with a hydraulic calcium aluminate cement formulations as described below in Example O. The calcium aluminate cement is preferably present in the composition in the range of about 1 to about 20% by weight.

It is also recognized that various additives such as, for example, pigments, dyes, plasticizers, softening agents, humectants, lubricants, waxes, radiopaque materials, heat and light stabilizers can be added to the composition of this invention.

For example, conventional filler materials may be added to the composition. For example, inorganic fillers, which can be naturally-occurring or synthetic, can be added. Such materials include, but are not limited to, zinc oxide, silica, titanium dioxide, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, and talc. Mixtures of the above-described filler materials also can be used in the composition if desired. Such filler materials are typically present in the composition in the range of about 10 to about 80% by weight.

The improved gutta-percha/Dentalcrete/hydroxylapatite composition of this invention is in the form of a rubbery-like material having good viscosity and handling properties. The improved composition may have a tapered conical shape similar to conventional gutta-percha cones used today. Tapered cones comprising the gutta-percha/Dentalcrete/hydroxylapatite composition may be fitted in root canals using standard endodontic obturator instruments. In other embodiments, the composition has been coated on a plastic endodontic carrier comprising a tapered shaft and upper handle portion. Particularly, the improved composition may be used in place of the gutta-percha composition presently used on THERMAFIL endodontic obturators (Dentsply Tulsa Dental Specialties).

In a method for sealing a tooth root canal, a sealing composition comprising a mixture of about 10% to about 50% by weight of gutta-percha and about 1% to about 30% by weight of Dentalcrete material can be first provided. The root canal in the tooth that will be filled is prepared following conventional techniques. Then, the sealing composition is introduced into the root canal, compacted, and allowed to harden and seal the canal.

It is expected that the improved gutta-percha/Dentalcrete/hydroxylapatite composition of this invention should provide an enhanced bonding to root canal sealers and to dentin itself. Bonding of dentin to sealer to gutta-percha has been a topic of great concern to endodontists in the prevention of bacterial migration in obturated, root-canal treated teeth. The hydrophilic nature of the Dentalcrete is expected to enhance the reactivity of the present invention with the moist dentin, perhaps eliminating the need for sealer. Alternatively, the present invention is expected to have enhanced bonding with the root canal sealers used. Thus, it is expected that the improved gutta-percha/Dentalcrete/hydroxylapatite composition of this invention should provide an improved barrier to bacterial and fluid leakage in the root canal system of a tooth. The composition should effectively seal off communication pathways between the root canals and surrounding tissue when used with a sealer. As a result, bacterial migration into the root canal system should be prevented.

In some cases of root canal therapy, some of the gutta-percha is extruded past the apex of a tooth. The gutta-percha can be an irritant and cause residual discomfort until the body resorbs the material over a period of months. It is expected that the composition of this invention should have good biocompatibility with the root canal system and promote normal healing of the bone and tissue surrounding the root tip, particularly if any of the material is extruded past the apex. The composition should enhance the growth of new bone and tissue surrounding the root tip area if an infection is present.

The invention is further illustrated by the compositions described in the following Examples, but these Examples should not be construed as limiting the scope of the invention.

EXAMPLES

In the following Examples, the term, Dentalcrete refers to a material comprising about 20% to about 80% tricalcium silicate ($3CaO \cdot SiO_2$); about 20% to about 50% dicalcium silicate ($2CaO \cdot SiO_2$); about 1% to about 20% tricalcium aluminate ($3CaO \cdot Al_2O_3$), about 1% to about 20% tetracalcium aluminoferrite ($4CaO \cdot Al_2O_3 \cdot Fe_2O_3$); about 1 to about 20% calcium sulfate dihydrate ($CaSO_4 \cdot 2H_2O$), and about 1 to about 50% radiopaque component, unless otherwise indicated. All percentages are by weight, unless otherwise indicated.

In some of the following Examples, the Dentalcrete material is referred to as containing finely milled or extra-finely milled particles. These terms are as used herein to refer to particles milled to the approximate dimensions as show in Table 1.

TABLE 1

| | (μm) | | |
|---|---|---|---|
| | Min. | Med. | Max. |
| Before Processing | 0.16 | 10.5 | 63.2 |
| Fine | 0.16 | 8.0 | 56.4 |
| Extra-Fine | 0.11 | 3.0 | 11.6 |

Example A

In this Example A, the following composition was prepared.

| Component | Weight Percentage (Wt. %) |
|---|---|
| Pure Gutta-percha | 22.50 |
| Dentalcrete (with 20% bismuth oxide) | 5.00 |
| Zinc Oxide | 55.05 |
| D & C Yellow No. 10 Lake | 0.80 |
| D & C Red No. 30 Lake | 0.48 |

-continued

| Component | Weight Percentage (Wt. %) |
|---|---|
| Stearic Acid UDM | 1.47 |
| Santonox TBMC | 0.44 |
| Barium Sulfate | 5.68 |
| Polyethylene Glycol 400 | 2.99 |
| Paraffin Wax 140/145 | 3.73 |
| Zinc Stearate | 1.86 |

Example B

In this Example B, a composition similar to the composition described in Example A was prepared, except the composition did not contain any barium sulfate.

| Component | Weight Percentage (Wt. %) |
|---|---|
| Pure Gutta-percha | 22.50 |
| Dentalcrete (with 20% bismuth oxide) | 15.89 |
| Zinc Oxide | 48.98 |
| D & C Red No. 30 Lake | 0.48 |
| Stearic Acid UDM | 1.50 |
| Santonox TBMC | 0.45 |
| Polyethylene Glycol 400 | 1.34 |
| Paraffin Wax 140/145 | 1.93 |
| Zinc Stearate | 1.93 |

Example C

In this Example C, a composition similar to the composition described in Example A was prepared, except the composition did not contain Dentalcrete with 20% bismuth oxide or barium sulfate. Instead, Dentalcrete composed of extra finely milled calcium compound particles and 40% bismuth oxide was used in the formulation.

| Component | Weight Percentage (Wt. %) |
|---|---|
| Pure Gutta-percha | 21.01 |
| Extra finely milled Dentalcrete (with 40% bismuth oxide) | 5.58 |
| Zinc Oxide | 61.86 |
| D & C Yellow No. 10 Lake | 0.78 |
| D & C Red No. 30 Lake | 0.47 |
| Stearic Acid UDM | 1.45 |
| Santonox TBMC | 0.43 |
| Polyethylene Glycol 400 | 2.93 |
| Paraffin Wax 140/145 | 3.66 |
| Zinc Stearate | 1.83 |

Example D

In this Example D, a composition similar to the composition described in Example A was prepared, except this composition contained a greater amount of gutta-percha and Dentalcrete (with 20% bismuth oxide).

| Component | Weight Percentage (Wt. %) |
|---|---|
| Pure Gutta-percha | 24.08 |
| Dentalcrete (with 20% bismuth oxide) | 10.00 |
| Zinc Oxide | 52.00 |
| D & C Yellow No. 10 Lake | 0.73 |
| D & C Red No. 30 Lake | 0.49 |
| Stearic Acid UDM | 1.50 |
| Santonox TBMC | 0.45 |
| Barium Sulfate | 2.00 |
| Polyethylene Glycol 400 | 3.04 |
| Paraffin Wax 140/145 | 3.81 |
| Zinc Stearate | 1.90 |

Example E

In this Example E, a composition similar to the composition described in Example A was prepared, except the composition did not contain Dentalcrete (with 20% bismuth oxide) or polyethylene glycol. Instead, Dentalcrete (with 40% bismuth oxide) was used in the formulation.

| Component | Weight Percentage (Wt. %) |
|---|---|
| Pure Gutta-percha | 24.13 |
| Dentalcrete (with 40% bismuth oxide) | 10.00 |
| Zinc Oxide | 55.22 |
| D & C Red No. 30 Lake | 0.51 |
| Stearic Acid UDM | 1.58 |
| Santonox TBMC | 0.47 |
| Barium Sulfate | 6.09 |
| Zinc Stearate | 2.00 |

Example F

In this Example F, a composition similar to the composition described in Example A was prepared, except the composition did not contain Dentalcrete (with 20% bismuth oxide) or barium sulfate. Instead, extra fine Dentalcrete (with 40% bismuth oxide) was used in the formulation.

| Component | Weight Percentage (Wt. %) |
|---|---|
| Pure Gutta-percha | 22.00 |
| Extra finely milled Dentalcrete with 40% bismuth oxide) | 20.00 |
| Zinc Oxide | 46.00 |
| D & C Red No. 30 Lake | 1.00 |
| Stearic Acid UDM | 1.50 |
| Santonox TBMC | 0.50 |
| Polyethylene Glycol 400 | 3.00 |
| Paraffin Wax 140/145 | 4.00 |
| Zinc Stearate | 2.00 |

Example G

In this Example G, a composition similar to the composition described in Example A was prepared, except the composition did not contain Dentalcrete (with 20% bismuth oxide). Instead, pre-reacted Dentalcrete was used in the formulation. The pre-reacted material was prepared by mixing the cement with water, allowing it to react, and grinding it again to a fine powder.

| Component | Weight Percentage (Wt. %) |
| --- | --- |
| Pure Gutta-percha | 22.50 |
| Pre-Reacted Dentalcrete powder | 5.00 |
| Zinc Oxide | 55.05 |
| D & C Yellow No. 10 Lake | 0.80 |
| D & C Red No. 30 Lake | 0.48 |
| Stearic Acid UDM | 1.47 |
| Santonox TBMC | 0.44 |
| Barium Sulfate | 5.68 |
| Polyethylene Glycol 400 | 2.99 |
| Paraffin Wax 140/145 | 3.73 |
| Zinc Stearate | 1.86 |

Example H

In this Example H, a composition similar to the composition described in Example A was prepared, except the composition did not contain Dentalcrete (with 20% bismuth oxide) or barium sulfate. Instead, pre-reacted Dentalcrete and un-reacted extra fine Dentalcrete with 40% bismuth oxide) was used in the formulation.

| Component | Weight Percentage (Wt. %) |
| --- | --- |
| Pure Gutta-percha | 22.00 |
| Extra finely milled Dentalcrete with 40% bismuth oxide) | 10.00 |
| Pre-Reacted Dentalcrete (extra finely milled particles with 40% bismuth oxide) | 20.00 |
| Zinc Oxide | 36.00 |
| D & C Red No. 30 Lake | 1.00 |
| Stearic Acid UDM | 1.50 |
| Santonox TBMC | 0.50 |
| Polyethylene Glycol 400 | 3.00 |
| Paraffin Wax 140/145 | 4.00 |
| Zinc Stearate | 2.00 |

Example I

In this Example I, a composition similar to the composition described in Example A was prepared, except the composition also contained extra fine Dentalcrete with 40% bismuth oxide).

| Component | Weight Percentage (Wt. %) |
| --- | --- |
| Pure Gutta-percha | 22.00 |
| Dentalcrete (with 20% bismuth oxide) | 10.00 |
| Extra finely milled Dentalcrete (with 40% bismuth oxide) | 10.00 |
| Zinc Oxide | 46.00 |
| D & C Red No. 30 Lake | 1.00 |
| Stearic Acid UDM | 1.50 |
| Santonox TBMC | 0.50 |
| Polyethylene Glycol 400 | 3.00 |
| Paraffin Wax 140/145 | 4.00 |
| Zinc Stearate | 2.00 |

Example J

In this Example J, a composition similar to the composition described in Example A was prepared, except the composition also contained hydroxylapatite and extra fine Dentalcrete with 40% bismuth oxide).

| Component | Weight Percentage (Wt. %) |
| --- | --- |
| Pure Gutta-percha | 22.00 |
| Dentalcrete (with 20% bismuth oxide) | 10.00 |
| Hydroxylapatite | 10.00 |
| Extra finely milled Dentalcrete with 40% bismuth oxide) | 10.00 |
| Zinc Oxide | 36.00 |
| D & C Red No. 30 Lake | 1.00 |
| Stearic Acid UDM | 1.50 |
| Santonox TBMC | 0.50 |
| Polyethylene Glycol 400 | 3.00 |
| Paraffin Wax 140/145 | 4.00 |
| Zinc Stearate | 2.00 |

Example K (Comparative)

In this Example K, a pure gutta-percha composition was prepared with no Dentalcrete or hydroxylapatite materials.

| Component | Weight Percentage (Wt. %) |
| --- | --- |
| Pure Gutta-percha | 19.60 |
| Zinc Oxide | 36.00 |
| D & C Yellow No. 10 Lake | 0.79 |
| D & C Red No. 30 Lake | 0.37 |
| Stearic Acid UDM | 0.80 |
| Santonox TBMC | 0.40 |
| Barium Sulfate | 7.86 |
| Polyethylene Glycol 400 | 0.98 |

Example L (Comparative)

In this Example L, a pure gutta-percha composition was prepared with no Dentalcrete or hydroxylapatite materials.

| Component | Weight Percentage (Wt. %) |
| --- | --- |
| Pure Gutta-percha | 22.51 |
| Zinc Oxide | 60.05 |
| D & C Yellow No. 10 Lake | 0.80 |
| D & C Red No. 30 Lake | 0.48 |
| Stearic Acid UDM | 1.47 |
| Santonox TBMC | 0.44 |
| Barium Sulfate | 5.68 |
| Polyethylene Glycol 400 | 2.99 |
| Paraffin Wax 140/145 | 4.00 |
| Zinc Stearate | 2.00 |

Example M

In this Example M, a pure gutta-percha composition was prepared with Dentalcrete material. This material was formed into tapered cones. These cones were softened and applied to plastic carriers to form experimental obturators like Thermafil obturators. When used by an endodontist, no differences could be determined between the gutta-percha/Dentalcrete cones and ordinary Thermafil obturators.

Example N

| Component | Weight Percentage (Wt. %) |
|---|---|
| Gutta-percha | 24.5 |
| Zinc Oxide | 66.5 |
| Titanium oxide | 1 |
| Butylated hydroxyl toluene (BHT) | 340 ppm |
| Bisphenol A diglycidyl ether | <0.3% |
| Zinc Stearate | 160 ppm |
| Dentalcrete (with no radiopaque component added) | 7.9 |

In this Example N, a pure gutta-percha composition was prepared with Dentalcrete material that contained only calcium silicates.

| Component | Weight Percentage (Wt. %) |
|---|---|
| Gutta-percha | 24.5 |
| Zinc Oxide | 66.5 |
| Titanium oxide | 1 |
| Butylated hydroxyl toluene (BHT) | 340 ppm |
| Bisphenol A diglycidyl ether | <0.3% |
| Zinc Stearate | 160 ppm |
| Dentalcrete (Di- or tri-calcium silicate only) | 7.9 |

Example O

In this Example O, a pure gutta-percha composition was prepared with different Dentalcrete materials containing calcium aluminate material and other additives.

| Component | Weight Percentage (Wt. %) |
|---|---|
| Gutta-percha | 24.5 |
| Zinc Oxide | 66.5 |
| Titanium oxide | 1 |
| Butylated hydroxyl toluene (BHT) | 340 ppm |
| Bisphenol A diglycidyl ether | <0.3% |
| Zinc Stearate | 160 ppm |
| Calcium aluminate ($CaAl_2O_4$) cement formulations prepared from the ingredients described below in Table 2) | 7.9 |

TABLE 2

Calcium Aluminate Cement Formulations

| | Calcium aluminate formulations | | |
|---|---|---|---|
| | 1 | 2 | 3 |
| $Al_2O_3$ & $TiO_2$ | 38-40 | 46.5 | 57.4 |
| CaO | 37-39 | 35.5 | 34.2 |
| $SiO_2$ | 3-5 | 8.5 | 5.7 |
| $Fe_2O_3$ + FeO | 15-18 | 6 | 1.2 |

The phases are widely variable in these calcium aluminate cement formulations and include: Monocalcium aluminate, $CaAl_2O_4$, (35 to 70%), Dodecacalcium hepta-aluminate, $12CaO \cdot 7Al_2O_3$, (0 to 10%), Monocalcium dialuminate, $CaO \cdot 2Al_2O_3$, (0 to 30%), Belite, $Ca_2SiO_4 \cdot$ (0 to 7%), Gehlenite $Ca_2Al_2SiO_7$ (1 to 14%), calcium alumino ferrite $Ca_2(Al, Fe)_2O_5$, (0 to 24%), $TiO_2$ (0.1 to 2%), and alumina (0 to 33%).

What is claimed is:

1. A composition for sealing a tooth root canal, comprising a mixture of about 10% to about 50% by weight of gutta-percha and about 1% to about 30% by weight of Dentalcrete material,
    wherein the Dentalcrete material comprises tricalcium silicate, dicalcium silicate, tricalcium aluminate, tetracalcium aluminoferrite, calcium sulfate dihydrate, and radiopaque component, and
    wherein the radiopaque component is selected from the group consisting of bismuth oxide, tantalum oxide. cerium oxide tin oxide, zirconium oxide compounds and radiopaque glasses containing tantalum, barium and strontium, and mixtures thereof.

2. The composition of claim 1, further comprising about 1 to about 20% by weight of hydroxylapatite.

3. The composition of claim 1, wherein the Dentalcrete material comprises about 20 to about 80 wt. % tricalcium silicate; about 20 to about 50 wt. % dicalcium silicate; about 1 to about 20 wt. % tricalcium aluminate, about 1 to about 20 wt. % tetracalcium aluminoferrite; about 1 to about 15 wt. % calcium sulfate dihydrate, and about 1 to about 50 wt. % radiopaque component.

4. The composition of claim 1, wherein the Dentalcrete material is in the form of powder particulate having an average particle size in the range of about 1 µm to about 40 µm.

5. The composition of claim 1, wherein the Dentalcrete material is in the form of powder particulate having an average particle size in the range of about 1 µm to about 15 µm.

6. The composition of claim 1, further comprising about 1 to about 20% by weight of calcium aluminate cement.

7. A method of sealing a tooth root canal, comprising the steps of:
    a) providing a sealing composition comprising a mixture of about 10% to about 50% by weight of gutta-percha and about 1% to about 30% by weight of Dentalcrete material;
    b) preparing the root canal in the tooth to be filled; and
    c) introducing the sealing composition into the root canal, compacting it and allowing the composition to harden and seal the root canal,
    wherein the Dentalcrete material comprises tricalcium silicate, dicalcium silicate, tricalcium aluminate, tetracalcium aluminoferrite. calcium sulfate dihydrate, and radiopaque component. and
    wherein the radiopaque component is selected from the group consisting of bismuth oxide, tantalum oxide, cerium oxide tin oxide, zirconium oxide compounds and radiopaque glasses containing tantalum, barium and strontium. and mixtures thereof.

8. The method of claim 7, wherein the composition further comprises about 1 to about 20% by weight of hydroxylapatite.

9. The method of claim 7, wherein the Dentalcrete material comprises about 20 to about 80 wt. % tricalcium silicate; about 20 to about 50 wt. % dicalcium silicate; about 1 to about 20 wt. % tricalcium aluminate, about 1 to about 20 wt. % tetracalcium aluminoferrite; about 1 to about 15 wt. % calcium sulfate dihydrate, and about 1 to about 50 wt. % radiopaque component.

10. The method of claim 7, wherein the Dentalcrete material is in the form of powder particulate having an average particle size in the range of about 1 µm to about 40 µm.

11. The method of claim 7, wherein the Dentalcrete material is in the form of powder particulate having an average particle size in the range of about 1 µm to about 15 µm.

* * * * *